United States Patent [19]

Columbus

[11] 4,254,083

[45] Mar. 3, 1981

[54] STRUCTURAL CONFIGURATION FOR TRANSPORT OF A LIQUID DROP THROUGH AN INGRESS APERTURE

[75] Inventor: Richard L. Columbus, Rochester, N.Y.

[73] Assignee: Eastman Kodak Company, Rochester, N.Y.

[21] Appl. No.: 59,924

[22] Filed: Jul. 23, 1979

Related U.S. Application Data

[63] Continuation-in-part of Ser. No. 954,689, Oct. 25, 1978.

[51] Int. Cl.³ ...................... G01N 33/00; G01N 33/48

[52] U.S. Cl. .................................... 422/55; 23/230 B; 422/56; 422/58; 422/100; 435/4; 435/310

[58] Field of Search .................................... 422/55-58, 422/68, 99, 100; 435/4, 310; 23/230 R, 230 B; 356/244

[56] References Cited

U.S. PATENT DOCUMENTS

| | | | |
|---|---|---|---|
| 3,690,836 | 9/1972 | Buissiere et al. | 422/56 |
| 3,783,696 | 1/1974 | Coleman | 422/100 X |
| 3,891,507 | 6/1975 | Breuer | 422/58 X |
| 3,992,158 | 11/1976 | Przybylowicz et al. | 422/57 |

FOREIGN PATENT DOCUMENTS

| | | | |
|---|---|---|---|
| 2396299 | 1/1979 | France | 23/230 B |

*Primary Examiner*—Arnold Turk

*Attorney, Agent, or Firm*—Dana M. Schmidt

[57] ABSTRACT

A device is disclosed that includes an ingress aperture which provides improved transport of a drop of liquid, from an exterior surface of the device to the device interior. Means are provided at the intersection of the aperture sidewall and the exterior surface for urging a drop deposited thereon to move into contact with the aperture sidewall and thus into the aperture.

19 Claims, 5 Drawing Figures

FIG. 4
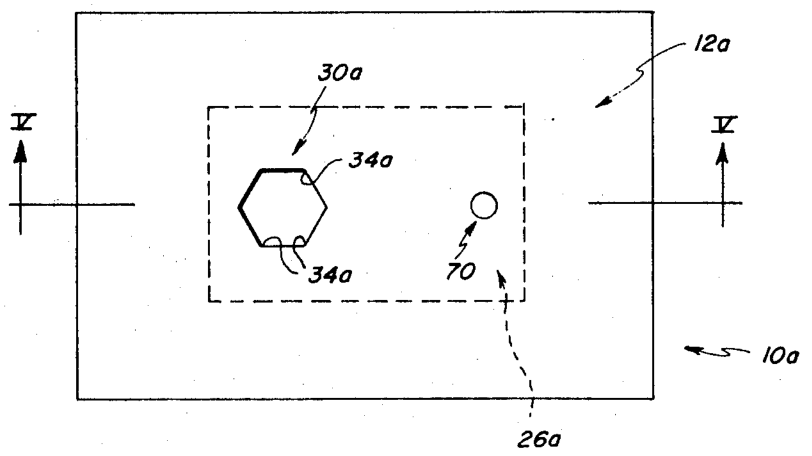
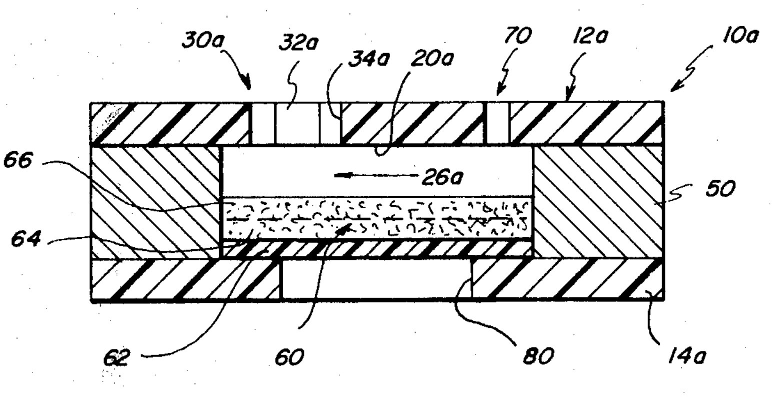
FIG. 5

STRUCTURAL CONFIGURATION FOR TRANSPORT OF A LIQUID DROP THROUGH AN INGRESS APERTURE

RELATED APPLICATIONS

This application is a continuation-in-part application of U.S. application Ser. No. 954,689, filed on Oct. 25, 1978, entitled "Liquid Transport Device and Method".

BACKGROUND OF THE INVENTION (1) Field of the Invention

This invention is directed to a device and method for transport of a liquid drop through an ingress aperture, e.g., into a transport zone prior to processing of the liquid. In a preferred embodiment, such aperture cooperates with opposed surfaces located within the device which provide for capillary flow of liquid within a transport zone. One of the surfaces can include a reagent-containing layer suitable for a radiometric analysis of the liquid.

(2) State of the Prior Art

A number of liquid transport devices rely upon capillary flow of liquid between two spaced-apart surfaces to spread the liquid. For example, an enclosed capillary chamber can be provided by sealing a cover sheet, e.g., around its perimeter to a reagent layer laminated to a support so that the cover sheet is left spaced away from the reagent layer a distance suitable for capillary flow. At least two apertures are then provided in the chamber. One aperture provides for the introduction of drops of liquid, and the other for the venting of air as the capillary chamber is filled. Such a device is shown, e.g., in U.S. Pat. No. 3,690,836, issued on Sept. 12, 1972.

Prior to this invention, the ingress aperture for introduction of liquid into a device of the type described above has featured a smooth, curved sidewall, such as a cylindrical wall. Such apertures suffer the disadvantage that a drop of liquid that is not accurately placed on the cover sheet, i.e., is placed with its center outside the sidewall of the aperture, tends to stay outside the aperture rather than move into it. It is only when the center of the drop is deposited well within the aperture that the surface tension of the liquid drop forces the drop into the aperture in full contact with the sidewall. Particularly this has been a problem for cover sheets formed from materials that tend to be hydrophobic, i.e., that form with the liquid in question a liquid-vapor contact angle that is greater than 90°. For example, certain plastics are sufficiently hydrophobic that drops of liquid such as blood serum are more likely to remain on the cover sheet than to flow into a cylindrical aperture in the sheet.

(3) Related Applications

U.S. application Ser. No. 059,816 filed on July 23, 1979, entitled *Electrode-Containing Device With Capillary Transport Between Electrodes* discloses liquid transport devices that function as a bridge between two electrodes, the liquid access apertures in one embodiment being a hexagon. U.S. application Ser. No. 954,689, filed on Oct. 25, 1978, entitled "Liquid Transport Device and Method," discloses such a hexagonal aperture for use in a liquid transport device in general.

SUMMARY OF THE INVENTION

This invention concerns the discovery that the ingress aperture of such devices can be predeterminedly shaped to be more effective in urging applied drops into it than previous apertures of the type having a sidewall comprising a smooth, curved surface, e.g., a cylinder.

More specifically, there is provided an improved liquid transport device comprising an exterior, drop-receiving surface, means interior of said surface for transporting the liquid through a zone, and an ingress aperture comprising an internal sidewall fluidly connecting the surface and the interior transporting means. The improvement features, in at least the intersection of the exterior surface and the sidewall, at a predetermined location, means for substantially urging a portion of a drop of liquid deposited on the surface to move into contact with the sidewall.

Such a device is particularly useful in introducing liquid into a transport zone between two opposed transport surfaces spaced apart a distance effective to induce capillary flow of the liquid between the transport surfaces.

Thus, in accordance with the present invention, there is provided a device having a drop-centering aperture for the improved conveyance of a drop of liquid from an exterior surface to an interior liquid transport zone of the device.

It is a significant aspect of the invention that aperture geometry facilitates such drop-centering.

In yet another related aspect of the invention, a test device for radiometric detection of an analyte is provided with a self-centering aperture.

Other features and advantages will become apparent upon reference to the following Description of the Preferred Embodiments when read in light of the attached drawings.

BRIEF DESCRIPTION OF THE DRAWINGS

FIG. 4 is a plan view of a preferred embodiment of the invention; and

FIG. 5 is a sectional view taken generally along the plane of line V—V of FIG. 4.

DESCRIPTION OF THE PREFERRED EMBODIMENTS

The device and method of this invention are described in connection with preferred embodiments featuring the capillary transport of biological liquids and particularly blood serum, between two opposed surfaces. In addition, the device and method can be applied to any liquid a drop of which is to be carried through an ingress aperture from an exterior surface to a transport means for transporting the liquid for any end use. For example, industrial liquids can be so transported.

Figure 1:
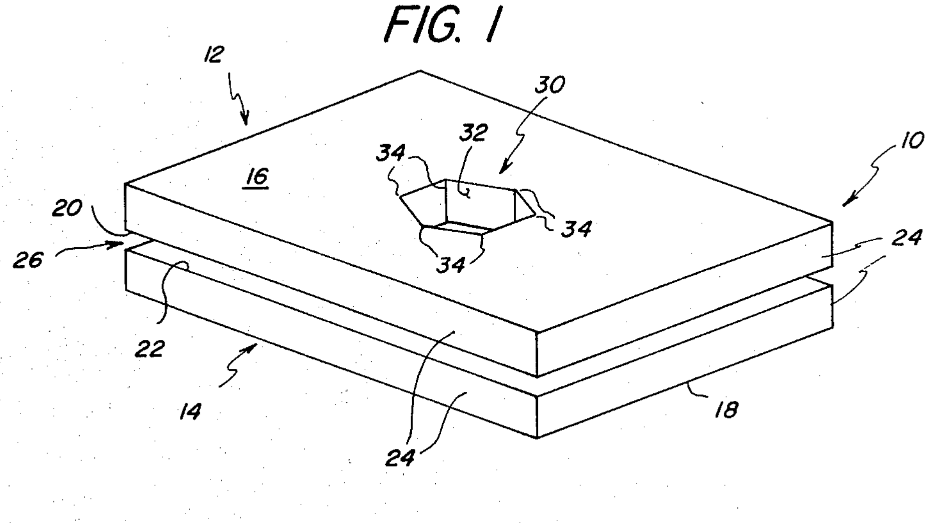
FIG. 1 is an enlarged dimetric view of a device prepared in accordance with the invention.

A device 10 constructed in accordance with one embodiment of the invention comprises, FIG. 1, two members 12 and 14 each having an exterior surface 16 and 18, respectively, and interior, opposed surfaces 20 and 22, respectively. Edge surfaces 24 define the limits of extension of the members. Surfaces 20 and 22 are spaced apart a distance "x", FIG. 2, that is effective to induce capillary flow of liquid between the surfaces, as is described in the aforesaid commonly-owned applications. In this manner the spaced-apart surfaces 20 and 22 define a transport zone 26 and act as means for transporting introduced liquid between the surfaces. As will be readily apparent, a range of values for "x" is permissible, and the exact value depends upon the liquid being transported.

Figure 2:
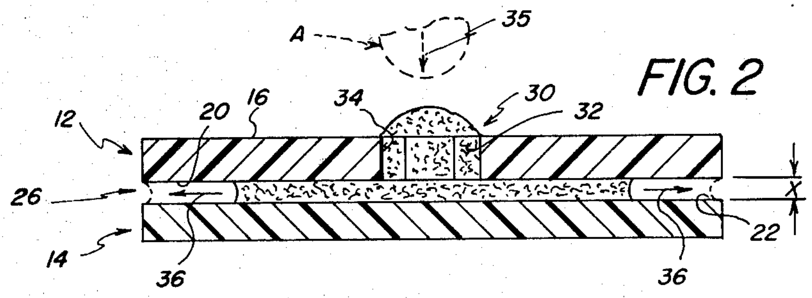
FIG. 2 is an elevational view in section through the aperture of the cover sheet, demonstrating the operation of the device.

Surfaces 20 and 22 can each be smooth, FIGS. 1 and 2, or provided with a variety of surface configurations such as parallel grooves, the grooves of one surface being aligned or at a positive angle with respect to the grooves of the other.

A preferred means for introducing a drop of liquid into zone 26 is an aperture 30 extending from surface 16 to surface 20, through member 12. The aperture comprises a sidewall 32 extending between the surfaces. The preferred largest flow-through dimension of aperture 30, measured as an outside diameter, is one which is about equal to the greatest diameter of the expected drop. The drop diameter in turn is dictated by the volume and surface tension of the drop. The volume of the drop should be adequate to fill transport zone 26 to the extent desired. For uses such as clinical analysis as herein described, a convenient drop volume is about 10 $\mu l$ . Thus, since a 10 $\mu l$ drop of fluid having 70 dynes/cm surface tension has a diameter of about 0.26 cm, the largest flow-through dimension, measured as an outside diameter, FIG. 1, is preferably about 0.26 cm.

In accordance with one aspect of the invention, the intersection of surface 16 and sidewall 32 is provided with means that encourage the selected drop of liquid deposited or received on surface 16 generally at aperture 30 to move into contact with the entire perimeter of sidewall 32. More specifically, sidewall 32 is shaped so as to comprise a plurality of surfaces that intersect, at least with surface 16, at predetermined locations to form a plurality of interior corners 34. As used herein, "predetermined location" or "locations" means locations deliberately chosen, and distinguishes the claimed invention from cylindrical apertures which inadvertently or accidentally have imperfections, such as microscopic corners, in the sidewall. Such accidental constructs are not capable of providing substantial urging of the drop into the aperture. As shown in FIG. 1, sidewall 32 comprises throughout its length, six sidewall surfaces and six such predetermined corners 34. Equal angles of such corners and equal widths of the intersecting surfaces are selected to provide a transverse, cross-sectional shape that is a regular hexagon, the preferred configuration.

In operation, FIG. 2, device 10 is placed in a drop-displacing zone adjacent to a source of drops, and a drop A of liquid such as blood serum or whole blood is dropped onto the device as a free-form drop or is touched off from a pendant surface, arrow 35, onto surface 16 generally at aperture 30. The surface 16 preferably is maintained in a generally horizontal orientation during this step. Corners 34 act to center the drop and urge it into contact with the surfaces of sidewall 32. It then moves down into zone 26 and into contact with surface 22, where capillary attraction further causes the liquid to spread throughout zone 26, arrows 36, to the position shown in phantom. Assuming sufficient volume in the drop, the spreading ceases at edge surfaces 24 which define an energy barrier to further capillary flow. Once the drop of liquid is so distributed, a variety of processing can be done to the liquid, as will be appreciated.

Thus the drop is applied to aperture 30 so as to contact one of the corners, to insure effective filling of the aperture. The effect is most pronounced when the center of gravity of the drop is positioned over the aperture, rather than the solid surface 16.

To vent air as the liquid advances within zone 26, means are provided within the device, such as the open space between members 12 and 14 along all or a portion of any one of edge surfaces 24. Alternatively, a second aperture, not shown, can be formed in either member 12 or 14.

The corners of the aperture, at the surface 16 where the drop is first applied, appear to act as centers of force which induce the drop to move into contact with sidewall 32 along its entire perimeter or circumference. That is, referring to FIG. 3, it is believed that the centering force $F_3$ of a drop A applied at one of the corners 34 is significantly greater than the corresponding centering force $F_1$ or $F_2$ that exists for a drop A′ placed at any adjacent location 38 or 39 spaced apart or away from a corner. At least one corner is needed for the effect. However, at least three corners 34 are preferred, as in FIG. 3, to insure a greater likelihood that the drop A will be in contact with a corner 34 when it contacts surface 16.

For a predetermined largest flow-through dimension of the sidewall 32 calculated as described above, the greater the number of corners that are created by the use of a corresponding number of intersecting surfaces, then the greater is the likelihood that the drop will contact a corner. However, as the number of corners is increased, so is the value of the interior angle of each corner, until eventually the sidewall 32 approaches a smooth, curved surface in shape wherein all the centering forces are equal, and the effect is lost. It has been found, therefore, that a preferred number of corners is between three and about ten. Highly preferred is six corners in a regular hexagon.

As a matter of practicality, the corners 34 will have a slight radius of curvature. For the corners to be effective, they each should have a radius of curvature that is no larger than about 0.4 mm.

Figure 3:
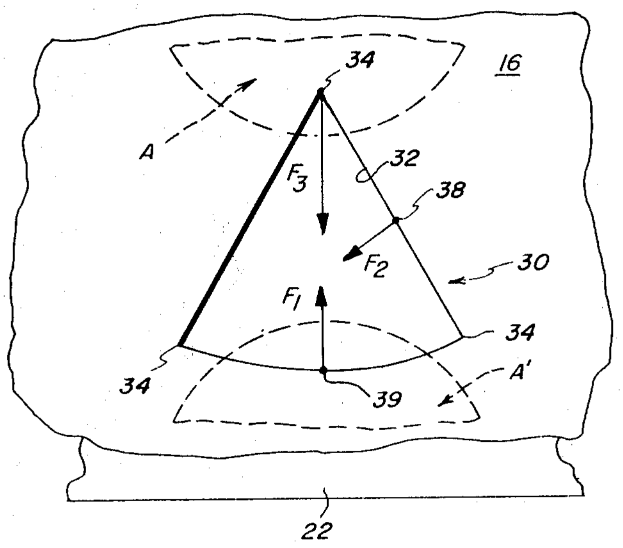
FIG. 3 is a fragmentary, diagrammatic plan view illustrating an effect of the invention.

Although flat or planar surfaces are preferred between the corners, they can also be continuously curved as shown, e.g., for surface 39, FIG. 3.

Although the centering mechanism of the corners is not fully understood, it is believed that the effect is due to forces that apply to the compound meniscus when the drop is located at a corner 34. As is well known, a compound meniscus is one in which the principal radii of curvature of the drop surface vary, depending on the location taken on the surface of the drop. If the drop is properly located at a corner, the compound meniscus forms a drop that extends laterally further out over the aperture than it does when not located at a corner, and the weight of this extension causes the drop to fall or otherwise move into contact with the perimeter of sidewall 32 and then through the aperture. Or, there is at the corner a greater tendency for the drop to wet the sidewall than would occur in the absence of a corner.

It will be readily appreciated that the centering force of corners 34 is needed primarily at the intersection of sidewall 32 and exterior surface 16. Thus, aperture 30 will function equally as well if sidewall 32 is smoothed out as it approaches surface 20 to form a cylinder, not shown.

In addition, it will also be appreciated that the presence of a capillary zone below aperture 30, and specifically surface 22 that contacts a drop in aperture 30, assists in metering the drop through aperture 30 and into the zone.

Members 12 and 14 can be formed from any suitable material, such as plastic as shown, or from metal.

In FIGS. 4 and 5, a preferred form of the device is one in which a transport chamber is formed for radiometric analysis of an analyte of a biological liquid such as blood. Parts similar to those previously described bear the same reference numeral to which the distinguishing suffix "a" is appended. Thus device 10*a* features a support member 14*a*, FIG. 5, a cover member 12*a*, a spacer member 50 used to adhere members 12*a* and 14*a* together, and a radiometrically detectable test element 60 disposed on support 14*a* spaced away from member 12*a* to define a transport zone 26*a*. The spacing between surface 20*a* and the test element is a capillary spacing to induce the drop that enters through aperture 30*a* to spread throughout the zone 26*a*. Preferably, the test element 60 abuts against the sidewalls of spacer member 50, and is held against member 14*a* by means such as adhesive.

Thus, the members 12*a*, 14*a* and 50 define a capillary transport chamber containing the test element 60 and having any convenient shape, such as a rectangular chamber when viewed in plan, FIG. 4.

Any suitable joining means can be applied between members 12*a* and 50, and members 50 and 14*a*. For example, a variety of adhesives can be used, or if all the members are plastic, ultrasonic welding or heat-sealing can be used.

Member 12*a* is provided with an access aperture 30*a* extending through the member from its exterior surface 16*a* to zone 26*a*, disposed directly above a portion of test element 60. At least that portion of the aperture's sidewall 32*a* that intersects with surface 16*a* is provided with corners 34*a* as described above. Preferably sidewall 32*a* is in the cross-sectional shape of a regular hexagon. An additional, cylindrically shaped aperture 70 in member 12*a* acts as a vent for expelled air.

A viewing aperture or port 80 is optionally provided in support member 14*a*, particularly when the latter member is not itself transparent.

Test element 60 comprises an optional transparent support 62, such as poly(ethylene terephthalate), and at least an absorbent layer 64 disposed on support 62. Such layer can have a variety of binder compositions, for example, gelatin, cellulose acetate butyrate, polyvinyl alcohol, agarose and the like, the degree of hydrophilicity of which depends upon the material selected. Gelatin is particularly preferred as it acts as a wetting agent to provide for uniform liquid flow through zone 26*a*. Support 62 can be omitted where adequate support for layer 64 can be obtained from support member 14*a*.

Additional layers such as a layer 66 can be disposed above layer 64 to provide a variety of chemistries or functions, such as to provide, either in layer 66 alone or together with layer 64, a reagent composition. Filtering, registration and mordanting functions can be provided also by such additional layers, such as are described in U.S. Pat. No. 4,042,335, issued on Aug. 16, 1977. Thus, layer 66 can comprise a reagent, such as an enzyme, and a binder of the same type as is used for layer 64.

As used herein, "reagent" in "reagent composition" means a material that is capable of interaction with an analyte, a precursor of an analyte, a decomposition product of an analyte, or an intermediate. Thus, one of the reagents can be a preformed, radiometrically detectable species that is caused by the analyte of choice to move out of a radiometrically opaque portion or layer of the element, such as layer 66, into a radiometrically transparent portion or layer, such as a registration layer.

The noted interaction between the reagents of the reagent composition and the analyte is therefore meant to refer to chemical reaction, catalytic activity as in the formation of an enzyme-substrate complex, or any other form of chemical or physical interaction, including physical displacement, that can produce ultimately a radiometrically detectable signal in the element 60. As is well known, radiometric detection includes both colorimetric and fluorimetric detection, depending upon the indicator reagent selected for the assay. The assay of the element is designed to produce a signal that is proportional to the amount of analyte that is present.

A wide variety of radiometric assays can be provided by element 60. Preferably, the assays are all oxygen-independent, as the flow of blood or blood serum into zone 26*a* tends to seal off element 60 from any additional oxygen. Typical analytes which can be tested include BUN, total protein, billirubin and the like. The necessary reagents and binder or vehicle compositions for the layers of element 60, such as layers 64 and 66, for these analytes can be those described in, respectively, U.S. Pat. Nos. 4,066,403, issued on Jan. 3, 1978; 4,132,528, issued on Jan. 2, 1979; and 4,069,016 or 4,069,017, issued on Jan. 17, 1978; and the like.

Quantitative detection of the change produced in element 60 by reason of the analyte of the test element is preferably made by scanning the element through port 80 with a photometer or fluorimeter. A variety of such instruments can be used, for example the radiometer disclosed in German OLS No. 2,755,334, published June 29, 1978, or the photometer described in U.S. Pat. No. 4,119,381, issued on Oct. 10, 1978.

The following is an illustrative example of the device shown in FIGS. 4 and 5.

Example

Members 12*a* and 14*a* are formed from polystyrene of a thickness 0.127 and 0.254 mm, respectively, member 50 being steel of a thickness 0.38 mm. The three members are sealed together by adhesives such as polybutyl acrylate adhesive obtainable from Franklin Chemical under trademark "Covinax." Apertures 30*a* and 70 in member 12*a* are about 8 mm apart on center, the outside diameter of the hexagon of aperture 30*a* being about 2.6 mm. View port 80 is about 5 mm in diameter. The capillary spacing between tested element 60 and member 12*a* is about 0.05 mm and the width of element 60 is about 11.5 mm.

For a test element 60 designed to detect total protein, in a 10 μl drop of blood serum, the following sequential layers are used:

| Layer | Composition | Amount |
|---|---|---|
| 62 | Gelatin-subbed poly(ethylene terephthalate) | 175 microns thick |
| 64 | poly(acrylamide-co-N-vinyl-2-pyrrolidone | 16.0 g/m$^2$ |
| | $CuSO_4 \cdot 5H_2O$ | 10.8 g/m$^2$ |
| | LiOH | 5.4 g/m$^2$ |
| | tartaric acid | 8.0 g/m$^2$ |

The invention has been described in detail with particular reference to certain preferred embodiments thereof, but it will be understood that variations and modifications can be effected within the spirit and scope of the invention.

What is claimed is:

1. In a liquid transport device comprising an exterior, drop-receiving surface, means interior of said surface for transporting the liquid through a zone, and an ingress aperture comprising an internal sidewall fluidly connecting said surface and said interior transporting means, the improvement wherein at least the intersection of said exterior surface and said sidewall includes at a predetermined location, means for substantially urging a portion of a drop of liquid deposited thereon to move into contact with said sidewall, said urging means including a surface configuration capable of forming a compound meniscus on a contacting liquid drop.

2. A device as defined in claim 1, wherein said surface configuration comprises an interior corner in the aperture sidewall at at least said exterior surface.

3. A device as defined in claim 1, wherein said intersection includes from 3 to about 10 of said urging means at spaced-apart locations.

4. A device as defined in claim 1, wherein said aperture has six of said urging means.

5. A device as defined in claim 1, wherein said transporting means includes two spaced-apart opposed surfaces at least one of which includes an absorbent layer containing at least one reagent capable of producing a radiometrically detectable signal when contacted by the liquid of the drop.

6. In a liquid transport device comprising an exterior surface, means interior of said surface for transporting the liquid through a zone, and an ingress aperture comprising an internal sidewall fluidly connecting said surface and said interior transporting means, the improvement wherein aperture has a transverse cross-sectional shape of a regular hexagon.

7. In a liquid transport device comprising an exterior surface, a capillary transport zone interior of said surface formed by interior, capillary-spaced surfaces of first and second wall members, one of said wall members including a liquid ingress aperture comprising a sidewall extending from said exterior surface to said transport zone, the improvement wherein at least the intersection of said exterior surface and said sidewall includes at a predetermined location, means for substantially urging liquid deposited on said surface to move into contact with said sidewall, said means including an interior corner in the aperture sidewall at at least said exterior surface.

8. A device as defined in claim 7, wherein said urging means comprises a plurality of predetermined, spaced-apart interior corners numbering from 3 to about 10.

9. A device as defined in claim 7, wherein said urging means comprises six generally equidistantly spaced interior corners in said aperture.

10. A device as defined in claim 7, wherein said urging means comprises said aperture having a transverse cross-sectional shape of a regular hexagon.

11. A device as defined in claim 7, wherein one of said interior surfaces includes an absorbent layer containing at least one reagent capable of producing a radiometrically detectable signal when contacted by the liquid of the drop.

12. In a liquid transport device comprising an exterior, drop-receiving surface, a capillary transport zone interior of said surface formed by interior, capillary-spaced surfaces of first and second members, one of said members including an ingress aperture extending from said exterior surface to said transport zone, the improvement wherein said aperture comprises from 3 to about 10 distinct sidewalls extending between said exterior surface and said interior surface of said one member, and intersecting to define from 3 to about 10 interior corners.

13. A device as defined in claim 12, wherein said aperture has six corners defined by six intersecting sidewalls.

14. A device as defined in claim 12, wherein said aperture has a transverse cross-sectional shape of a regular hexagon.

15. A device as defined in claim 12, wherein said other member interior surface is the exposed surface of an absorbent layer containing at least one reagent capable of producing a radiometrically detectable signal when contacted by the liquid.

16. A device as defined in claim 1, 7 or 12, wherein the liquid is a biological liquid.

17. A device as defined in claim 16, wherein said liquid is blood serum.

18. A device as defined in claim 1 or 6, wherein said transporting means comprises opposing surfaces of first and second wall members, spaced apart a distance effective to induce capillary flow of liquid introduced into said zone.

19. A test device for radiometric detection of an analyte of a liquid, comprising a support, a cover member spaced away from the support, one or more layers disposed sequentially on the support and containing at least one reagent composition in at least one of said layers, said composition being capable of producing a radiometrically detectable signal that is proportional to the quantity of the analyte, means for sealing said layers between said support and said cover member with a capillary space between the outermost one of said layers and said cover member, said space being effective to provide capillary flow of liquid between said cover member and said outermost layer, said cover member including a liquid ingress aperture and an air vent aperture spaced away from said access aperture, said ingress aperture having a sidewall extending through said cover member and comprising six surfaces intersecting to form six corners, whereby liquid placed in contact with said cover member at said ingress aperture is urged by said corners to enter the aperture and said capillary space.

* * * * *